(12) United States Patent
Mendrok-Edinger et al.

(10) Patent No.: US 11,931,444 B2
(45) Date of Patent: *Mar. 19, 2024

(54) TOPICAL COMPOSITION

(71) Applicant: DSM IP Assets B.V., Heerlen (NL)

(72) Inventors: Christine Mendrok-Edinger, Kaiseraugst (CH); Alexander Schlifke-Poschalko, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 408 days.

This patent is subject to a terminal disclaimer.

(21) Appl. No.: 16/981,788

(22) PCT Filed: Mar. 19, 2019

(86) PCT No.: PCT/EP2019/056876
§ 371 (c)(1),
(2) Date: Sep. 17, 2020

(87) PCT Pub. No.: WO2019/180038
PCT Pub. Date: Sep. 26, 2019

(65) Prior Publication Data
US 2021/0106511 A1   Apr. 15, 2021

(30) Foreign Application Priority Data
Mar. 20, 2018   (EP) .................... 18162872

(51) Int. Cl.
| | | |
|---|---|---|
| A61K 8/49 | (2006.01) | |
| A61K 8/04 | (2006.01) | |
| A61K 8/06 | (2006.01) | |
| A61K 8/31 | (2006.01) | |
| A61K 8/34 | (2006.01) | |
| A61K 8/37 | (2006.01) | |
| A61K 8/58 | (2006.01) | |
| A61Q 17/04 | (2006.01) | |

(52) U.S. Cl.
CPC .............. *A61K 8/49* (2013.01); *A61K 8/044* (2013.01); *A61K 8/062* (2013.01); *A61K 8/31* (2013.01); *A61K 8/345* (2013.01); *A61K 8/375* (2013.01); *A61K 8/58* (2013.01); *A61Q 17/04* (2013.01); *A61K 2800/412* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 6,030,607 A | 2/2000 | Linares | |
| 2014/0147397 A1 | 5/2014 | Berte' et al. | |
| 2015/0037379 A1* | 2/2015 | Mendrok-Edinger | ...................... A61Q 17/04 424/59 |
| 2015/0157996 A1* | 6/2015 | Dussaud | ................ A61Q 17/04 514/786 |

FOREIGN PATENT DOCUMENTS

| | | |
|---|---|---|
| EP | 1 317 918 | 6/2003 |
| JP | H09301825 | 11/1997 |
| JP | 2003-192557 | 7/2003 |
| JP | 2005-513091 | 5/2005 |
| JP | 2010-059136 | 3/2010 |
| JP | 2013-199443 | 10/2013 |
| JP | 2015-509925 | 5/2015 |
| JP | 2018-514529 | 6/2018 |
| WO | WO 02/39972 | 4/2002 |
| WO | 02/39972 | 5/2002 |

OTHER PUBLICATIONS

International Preliminary Report on Patentability, International Application No. PCT/EP2019/056876, dated Oct. 1, 2020.
International Search Report for PCT/EP2019/056876 dated May 14, 2019, 3 pages.
Written Opinion of the ISA for PCT/EP2019/056876 dated May 14, 2019, 6 pages.

* cited by examiner

*Primary Examiner* — David J Blanchard
*Assistant Examiner* — Sarah J Chickos
(74) *Attorney, Agent, or Firm* — NIXON & VANDERHYE P.C.

(57) ABSTRACT

The present invention relates to topical compositions comprising at least one polar oil and a micronized 1,4-di(benzoxazol-2'-yl)benzene having a mean particle size of at most 300 nm as well as to the use of such a micronized 1,4-di(benzoxazol-2'-yl)benzene to reduce the transfer of such oils to surfaces.

20 Claims, 1 Drawing Sheet

X-ray powder diffraction measurements
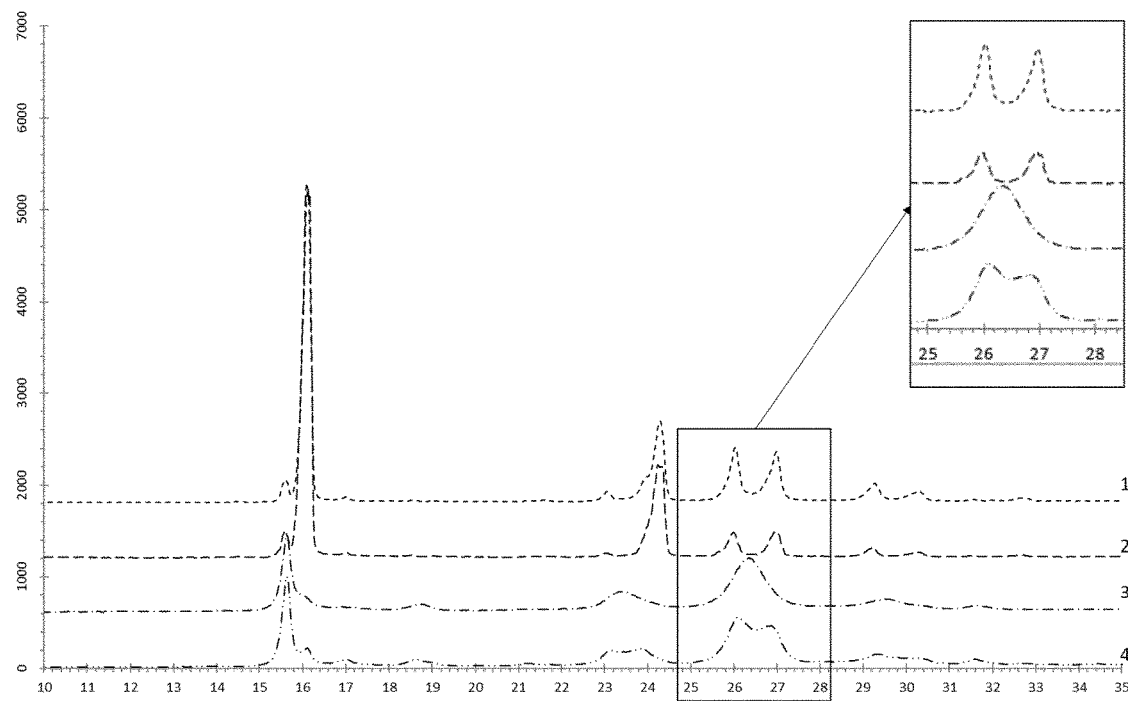
Legend:
x-axis: °2Theta (Cu K-alpha Radiation)
y-axis: Counts/s
lines 1 and 2: XRD of two different batches of crystalline DBO-200 (C)
lines 3 and 4: XRD of two different batches of amorphous DBO-200 (A)

TOPICAL COMPOSITION

This application is the U.S. national phase of International Application No. PCT/EP2019/056876 filed Mar. 19, 2019 which designated the U.S. and claims priority to EP Patent Application No. EP 18162872.8 filed Mar. 20, 2018, the entire contents of each of which are hereby incorporated by reference.

The present invention relates to topical compositions comprising at least one polar oil and a micronized 1,4-di(benzoxazol-2'-yl)benzene having a mean particle size of at most 300 nm as well as to the use of such a micronized 1,4-di(benzoxazol-2'-yl)benzene to reduce the transfer of such oils to surfaces.

Sun care products have evolved considerably over the years. Earlier formulations were intended to protect the user from UV-B radiation as was once thought that UV-B rays were the most important contributors to wrinkling, skin disease, and skin cancer. However, more recent studies have shown that UV-A radiation is equally or even more important in the development of solar damage and skin diseases, such as lupus erythematosus and melanoma and non-melanoma skin cancer. Thus, today's focus is towards eliminating as much of UVA (320-400 nm) and/or UVB (280-320 nm) light as possible. Consequently, there's a constantly increasing need for sun care products exhibiting high SPF's (Sun Protection Factor) and at the same time high UVA protection while being photostable.

Accordingly, today's sun care products comprise significant amounts of different UV-filter substances to fulfill the above-mentioned requirements. However, as many UV-filters are solids, polar oils are needed to solubilize these UV-filters to be able to incorporate them into the sun care products. Due to the high oil load such sun care products therefore often exhibit unpleasant sensorial properties which knowingly reduce customer acceptability and thus lead to a reduction of the amounts and/or times the product is applied to the skin, far below the recommended use level.

A further problem of such sun care products is that the material contained therein after application to a surface, particularly to the skin, is transferred to another surface when said surfaces are brought into contact with each other (also referred herein as 'material transfer'). Such a transfer is nega¬tive in two ways: First of all, the transfer of the material is not desired as it is re¬moved from the site of action, such as treating, moisturizing or protecting the skin; Secondly, the surface of contact is contaminated with said material such as in particular with oils which often results in staining of fabrics, such as clothes as well as in contamination of decorative or functional surfaces. The latter is not only negative in view of reduced functionality but also highly unwanted due to an unpleasant visual and/or aesthetic appearance. Particularly, displays of mobile phones, screens, spectacle glasses or touch screens are negatively affected by such material transfer as the material such as in particular the oils contained therein renders the surfaces smeary which is highly unwanted by the end consumer. Accordingly, there exist a great desire to reduce the transfer of topical sun care products and in particular the oils contained therein from surface to surface (in particular hard surfaces) when the surfaces are contacted.

Surprisingly, it has been found that topical compositions comprising at least one polar oil in combination with a micronized 1,4-di(benzoxazol-2'-yl)benzene having a mean particle size of at most 300 nm exhibit a significantly reduced material transfer to a contacted surface such as particularly a glass surface compared to compositions comprising a micronized 1,-di(benzoxazol-2'-yl)benzene having a mean particle size of more than 300 nm. This reduction is particularly pronounced when polar oils having a polarity index of 40 mN/m or less are used.

Thus, the invention relates in one aspect to topical compositions comprising at least one polar oil, wherein the composition further comprises a micronized 1,4-di(benzoxazol-2'-yl)benzene having a mean particle size of at most 300 nm.

The amount of each polar oil in the topical compositions according to the present invention is advantageously selected in the range from 1 to 30 wt.-%, more preferably in the range from 2 to 25 wt.-%, most preferably in the range from 3 to 20 wt.-%, such as in the range of 5 to 18 wt.-%, based on the total weight of the topical composition.

The amount of the micronized 1,4-di(benzoxazol-2'-yl)benzene (based on the active) in the topical compositions according to the present invention is advantageously selected in the range from 0.1 to 20 wt.-%, more preferably in the range from 0.2 to 15 wt.-%, most preferably in the range from 0.3 to 10 wt.-%, based on the total weight of the topical composition. Further suitable ranges are 0.15 to 10 wt.-%, 0.2 to 10 wt.-% and 0.5 to 10 wt.-%, based on the total weight of the topical composition.

The total amount of polar oil(s) in the topical compositions according to the present invention is advantageously selected in the range from 5 to 40 wt.-%, more preferably in the range from 6 to 30 wt.-%, most preferably in the range from 7 to 25 wt.-%, such as in the range of 8 to 20 wt.-%, based on the total weight of the topical composition.

The term 'topical' as used herein is understood here to mean external application to keratinous substances, which are in particular the skin, scalp, eyelashes, eyebrows, nails, mucous membranes and hair, preferably the skin.

The term "material transfer" as used herein refers to the mass transfer of the topical composition or some ingredients thereof when the topical composition is applied to a surface and afterwards said surface is brought in contact with a surface of a different object and separated again. By this contact some material is transferred from the first surface to the surface of the different object. The amount of material transferred can be determined by measuring the weight gain of the second object.

As the topical compositions according to the invention are intended for topical application, it is well understood that they comprise a physiologically acceptable medium, i.e. a medium compatible with keratinous substances, such as the skin, mucous membranes, and keratinous fibres. In particular the physiologically acceptable medium is a cosmetically acceptable carrier.

The term 'cosmetically acceptable carrier' refers to all carriers and/or excipients and/or diluents conventionally used in topical cosmetic compositions such as in particular in sun care products.

Examples of such cosmetic carriers, excipients and diluents as well as additives and active ingredients commonly used in the skin care industry which are suitable for use in the topical compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the excipients, diluents, adjuvants, additives etc. can, based on the desired product form and application, easily be determined by the skilled person.

The additional ingredients can either be added to the oily phase, the aqueous phase or separately as deemed appropriate.

In an advantageous embodiment, the topical compositions according to the present invention comprise from 50% to 99%, preferably from 60% to 98%, more preferably from 70% to 98%, such as in particular from 80% to 95% of a carrier, based on the total weight of the topical composition.

In a particular advantageous embodiment, the carrier consists furthermore of at least 40 wt.-%, more preferably of at least 50 wt.-%, most preferably of at least 55 wt.-% of water, such as in particular of 55 to 90 wt.-% of water.

The term 'polar oil' as used herein refers to any (lipophilic) substance which has a polarity index of less than 55 mN/m, more preferably of less than 50 mN/m, most preferably of 40 mN/m or less and which is liquid at ambient temperature (i.e. 25° C.). Preferably, in all embodiments of the present invention the polar oil has a polarity index of 40 mN/m or less as this further reduces the material transfer such as in particular the transfer of the respective oil(s). Even more preferably, the polarity index is selected in the range from 1 to 45 mN/m, more preferably in the range from 1 to 40 mN/m, such as from 4 to 37 mN/m or from 4 to 36 mN/m, most preferably in the range from 5 to 32 mN/m such as in the range from 8 to 30 mN/m.

Even more advantageously, in all embodiments of the present invention, the polarity index is selected in the range from 1 to 10 mN/m, more preferably in the range from 3 to 9 mN/m, most preferably in the range from 4 to 8 mN/m and/or in the range from 25 to 40 mN/m, more preferably in the range from 26 to 39 mN/m, most preferably in the range from 27 to 38 mN/m as this leads to a particular pronounced reduction of the material transfer such as of the oils.

The term "polarity index" is a parameter which is known to the person skilled in the art. The polarity of an oil is defined as the polarity index (interfacial tension) of the oil with respect to water. The interfacial tension, i. e. the polarity index, can be particularly determined using a ring tensiometer (e.g., Krüss K 10), which measures the interfacial tension in mN/m in analogy to the ASTM method D971-99a (2004).

Polar oils according to the present invention are well known to a person in the art and encompass in particular esters such as e.g. cocoglycerides (Myritol 331), di-C12-13 alkyl tartrate (Cosmacol ETI), di-C12-13 alkyl lactate (Cosmacol ELI), caprylic/capric triglycerides (Miglyol 812), isopropyl lauroyl sarcosinate (Eldew SL-205), pentaerytrityl tetraisostearate (Crodamol PTIS), PEG-2 diethylene hexanoate (Dermol 488), isostearyl isostearate (Prisorine 2039), dibutyl adipate (Cetiol B), stearyl heptanoate (Tegosoft SH), diisopropyl sebacate (DUB DIS), phenethyl benzoate (X-Tend 226), propylene glycol dicaprylate/dicaprate (Miglyol 840), tricaprylin (Trivent OCG), butylene glycol dicaprylate/dicaprate (Dermofeel BGC), isopropyl stearate, triheptanoin (Dermofeel TC-7), octyldodecyl myristate (Gatteefosse M.O.D.), isodecyl salicylate (Dermol IDSA), ethylhexyl palmitate (Tegosoft OP), diethylhexyl succinate (Crodamol OSU), dicaprylyl ether (Cetiol OE), isopropyl myristate, ethylhexyl benzoate (Finsolv EB), tridecyl isononanoate (Dermol 139), ethylhexyl isononanoate (Dermol 98), cetearyl isononanoate (Cetiol SN), isopropyl palmitate, diethylhexyl carbonate (Tegosoft DEC), isohexyl decanoate (Dermol IHD), isodecyl neopentanoate (DUB VCI 10), dicaprylyl carbonate (Crodamol DA), and diethyl adipate (DUB DEA) as well as mixtures thereof.

Such polar oils encompass as well alcohols such as e.g. diethylene glycol (Dermol 489), isostearyl alcohol (Prisorine 3531), butyloctanol (Isofol 12), butyldodecanol (Eutanol G), as well as in particular natural oils such as e.g. avocado oil, castor oil, macadamia nut oil, jojoba oil, as well as in particular polar silicone oils such as e.g. phenyl trimethicone (Dow Corning 558 Fluid), dimethicone (Wacker AK 100), cyclomethicone (Dow Corning Fluid 345), cyclopolydimethylsiloxane (Dow Corning Fluid 244), and Cyclopentasiloxane (Xiameter PMX-0245) as well as in particular alkanes such as isohexadecane, isododecane as well as mixtures thereof.

Preferred oils with a polarity index of between 40 and 50 mN/m is an oil selected from the group consisting of isoparaffin (C12-C14), polydecene, squalane, hydrogenated polyisobutene, isohexa¬decane, paraffin oil perliquidum, polydimethylsiloxane, isoeicosane, dioctylcyclohexane, ethoxydiglycol oleate, particularly from the group consisting of hydrogenated polyisobutene, isohexadecane and squalane.

Preferred oils with a polarity index of between 20 and 40 mN/m is an oil selected from the group consisting of paraffinum liquidum, cyclopentasiloxane, paraffin oil subliquidum, isocetyl palmitate, isocetyl stearate, dicaprylyl carbonate, octyl iso¬stearate, trimethylhexyl isononanoate, 2-ethylhexyl isononanoate, cetearyl isononanoate, dicaprylyl ether, dihexyl carbonate and octyl cocoate, particularly from the group consisting of di-caprylyl carbonate, isocetyl stearate and cetearyl isononanoate.

Preferred oils with a polarity index between 1 and 10 mN/m are di-C12-13 alkyl tartrate, or cocoglycerides.

Most preferred in all embodiments of the present invention are polar oils selected from the group consisting of isocetyl stearate, dicaprylyl carbonate, cetearyl isononanoate, C12-13 alkyl tartrate and cocoglycerides as well as mixtures thereof.

In a particular advantageous embodiment, the topical compositions according to the present invention comprise only polar oils having a polarity index selected in the range from 1 to 10 mN/m, more preferably in the range from 3 to 9 mN/m, most preferably in the range from 4 to 8 mN/m and/or in the range from 25 to 40 mN/m, more preferably in the range from 26 to 39 mN/m, most preferably in the range from 27 to 38 mN/m such as in particular polar oils selected from the group of isocetyl stearate, dicaprylyl carbonate, cetearyl isononanoate, C12-13 alkyl tartrate and cocoglycerides as well as mixtures thereof.

The term 'mean particle size' as used herein refers to the mean number-based particle size distribution $D_n50$ (also known as $D_n0.5$) as determined by laser diffraction e.g. with a Malvern Mastersizer 2000 (ISO 13320:2009).

In an advantageous embodiment, the micronized organic UV-filter according to the present invention exhibits a $D_n50$ in the range from 50 to 300 nm, more preferably in the range from 100 to 300 nm, most preferably in the range from 120 to 280 nm, such as in the range from 140 to 240 nm or in the range from 150 to 220 nm as determined by laser diffraction (Malvern Mastersizer 2000).

Preferably, in all embodiments of the present invention, the micronized 1,4-di(benzoxazol-2'-yl)benzene according to the present invention furthermore exhibits a $D_n10$ (also known as $D_n0.1$) in the range from 30 to 230 nm, more preferably in the range from 80 to 180 nm, most preferably in the range from 100 to 160 nm as determined by laser diffraction (Malvern Mastersizer 2000).

Preferably, in all embodiments of the present invention, the micronized 1,4-di(benzoxazol-2'-yl)benzene according to the present invention furthermore exhibits a $D_n90$ (also known as $D_n0.9$) in the range from 250 to 350 nm, more preferably in the range from 300 to 400 nm, most preferably in the range from 325 to 375 nm as determined by laser diffraction (Malvern Mastersizer 2000).

Particular advantageous micronized 1,4-di(benzoxazol-2'-yl)benzene according to the present invention exhibits a $D_n10$ in the range from 100 to 160 nm, a $D_n50$ in the range from 150 to 220 nm and a $D_n90$ in the range from 325 to 375 nm as determined by laser diffraction (Malvern Mastersizer 2000).

It is furthermore advantageous if the 1,4-di(benzoxazol-2'-yl)benzene according to the present invention is a solid amorphous form of 1,4-di(benzoxazol-2'-yl)benzene, as such solid amorphous forms surprisingly exhibits improved physical properties with regard to UV-absorption/protection, SPF contribution and formulation stability compared to the respective crystalline form.

The term "solid amorphous form," as used herein, refers to solid particles which are formed by fast formation/separation of a solid phase from a liquid phase in a solution or a mixture, so that the solid has no time to selectively form a crystal network and thus the obtained solid is in a predominantly disordered form (also referred to herein as 'solid amorphous 1,4-di(benzoxazol-2'-yl)benzene'), which form can be identified by XRPD analysis as illustrated herein. The solid amorphous 1,4-di(benzoxazol-2'-yl)benzene according to the present invention exhibits improved physical properties with regard to UV-absorption/protection, SPF contribution and formulation stability compared to the respective crystalline form.

The solid amorphous form of micronized 1,4 di(benzoxazol-2'-yl)benzene according to the present invention is characterized by a specific absorbance E 1/1 @ 320 nm of ≥750, preferably of ≥780, while the respective pure crystalline form exhibits a significantly lower specific absorbance E 1/1, i.e. a E 1/1 @ 320 nm of only 719. Thus, in a preferred embodiment, the solid amorphous form of 1,4 di(benzoxazol-2'-yl)benzene according to the present invention is characterized by a specific absorbance E 1/1 @ 320 nm of at least 750, more preferably of at least 780. Even more preferably the specific absorbance E 1/1 @ 320 nm is selected in the range from 780 to 850, most preferably in the range from 800 to 845.

The specific absorbance E1/1 (1 cm/1%) is well known to a person skilled in the art and is the (base line corrected) extinction corresponding to a concentration of a 1% (w/v) solution or dispersion of the tested compound at an optical thickness of 1 cm at lambda max (i.e. the wavelength in the absorption spectrum where the absorbance is maximum).

The solid amorphous form of the micronized 1,4-di(benzoxazol-2'-yl)benzene is furthermore characterized by an X-ray powder diffraction (XRPD) pattern substantially as depicted in FIG. 1, lines 3 and 4 which is substantially different to the one of crystalline 1,4-di(benzoxazol-2'-yl)benzene (FIG. 1, lines 1 and 2). As can be retrieved from FIG. 1, the crystalline form is characterized by an unambiguous base line separation of the peaks at 25-28 °2Theta (Cu K-alpha Radiation), while the solid amorphous form does not exhibit said base line separation. The X-ray diffraction patterns were recorded using a Bruker D8 Advance powder X-ray diffractometer in reflection (Bragg-Brentano) geometry with a LynxEye detector and Cu Kα radiation.

In another (or even in an additional) embodiment, the solid amorphous form of 1,4-di(benzoxazol-2'-yl)benzene can also be characterized by its differential scanning calorimetry (DSC) thermogram exhibiting an onset temperature in the range of about 345 to 351 and a heat capacity in the range of about 115-135 J/g. DSC endotherms were recorded using a Mettler Toledo DSC1 (Temperature range: 25° C. to 400° C. heating rate: 4° C./min) as outlined in the examples.

The solid amorphous form of micronized 1,4-di(benzoxazol-2'-yl)benzene according to the present invention is furthermore characterized by a ratio of its UVB to UVA absorbance, which is ranging from 0.40 to 0.55, more preferably from 0.44 to 0.54, most preferably from 0.47 to 0.51. The ratio is determined by measuring the UV-spectra of the micronized 1,4-di(benzoxazol-2'-yl)benzene dispersed in water at a concentration of 0.001% (w/v) and calculating the ratio by dividing the area-% from 290 to 319 nm (UVB) through the area-% from 320 to 400 nm (UVA).

The micronized 1,4-di(benzoxazol-2'-yl)benzene according to the present invention can be produced by standard micronization methods in the art as e.g. outlined in WO9522959 and WO9703643 which are included herein by reference.

The coarse particles of the 1,4-di(benzoxazol-2'-yl)benzene, i.e. particles having particle size of >350 nm can for example be prepared as outlined in example 1 of WO2002039972 or as illustrated in the examples of the present invention.

To obtain the micronized 1,4-di(benzoxazol-2'-yl)benzene according to the present invention, coarse particles, more preferably coarse particles of solid amorphous 1,4-di(benzoxazol-2'-yl)benzene, are micronized by conventional grinding methods in the art until a particle size with all the definitions and preferences as given herein is obtained, e.g. by grinding the coarse particles, preferably in the presence of a grinding aid and optionally further customary additives used in the preparation of micronized organic UV-filters, using known grinding apparatus, e.g. a jet, ball, vibration or hammer mill, preferably a high speed stirring mill. Preferably, modern ball mills are used; manufacturers of these types of mill are, for example, Netzsch (LMZ mill), Drais (DCP—Viscoflow or Cosmo), Bühler AG (centrifugal mills) or Bachhofer.

The term 'additive' as used herein refers to additives commonly used in micronization processes such as in particular in micronization processes to prepare aqueous dispersions of micronized, organic UV-filters. Preferred additives in all embodiments of the present invention are antifoam agents, wetting agents, salts, preservatives and thickeners. These additives can either be added before/during grinding or after grinding, e.g. to stabilize an aqueous dispersion of the micronized, 1,4-di(benzoxazol-2'-yl)benzene according to the present invention obtainable from the wet milling process.

It is well understood, that the micronized 1,4-di(benzoxazol-2'-yl)benzene according to the present invention is insoluble in common cosmetic oils, wherein the term 'insoluble' refers to a solubility at RT (i.e. ~22° C.) in common cosmetic oils such as e.g. $C_{12-15}$ alkyl benzoate, propyleneglycol, mineral oil but also in water of less than 0.01 wt.-%, preferably of less than 0.05 wt.-%, most preferably of less than 0.03 wt.-% and thus remains in a particular state after incorporation into a topical composition such as a sun care product.

The micronized 1,4-di(benzoxazol-2'-yl)benzene according to the present invention may be used in powder form or in the form of a dispersion of the micronized 1,4-di(benzoxazol-2'-yl)benzene. Preferably, in all embodiments of the present invention the micronized 1,4-di(benzoxazol-2'-yl)benzene is used in the form of an aqueous dispersion of the micronized 1,4-di(benzoxazol-2'-yl)benzene as e.g. directly obtainable by wet milling processes.

The amount of the micronized 1,4-di(benzoxazol-2'-yl) benzene according to the present invention in such aqueous dispersions is preferably selected in the range from 10 to 90 wt.-%, 20 to 80 wt.-% or 30 to 70 wt-%, more preferably in the range from 25 to 60 wt.-%, most preferably in the range from 25 to 55 wt.-%, such as in the range of 25 to 35 wt.-%, based on the total weight of the aqueous dispersion.

Preferably, in all embodiments is the use of an aqueous dispersion of micronized solid amorphous 1,4-di(benzoxazol-2'-yl)benzene with all the preferences and definitions as given herein.

It is well understood that such aqueous dispersions may contain customary additives commonly used in the preparation of micronized organic UV-filters such as in particular grinding aids, wetting agents, thickeners, anti-foam agents and salts as well as mixtures thereof. These additives can either be added before/during grinding or after grinding, e.g. to stabilize the aqueous dispersion.

The amount (total) of such additives in the aqueous dispersions according to the present invention is preferably selected in the range from 0.01 to 25 wt.-%, more preferably in the range from 2 to 20 wt.-%, most preferably in the range from 3 to 15 wt.-%, such as in the range from 5 to 10 wt.-%, based on the total weight of the aqueous dispersion.

Suitable grinding aids are surface-active ingredients, that can be used as dispersing agent such as in particular anionic, non-ionic, amphoteric and cationic surfactants as well as mixtures thereof.

Most preferred in all embodiments according to the invention the grinding aid is an alkyl poly-glucoside.

The term 'alkyl poly-glucoside (APG)' refers to a class of non-ionic surfactants having the generic formula $C_nH_{2+n}O(C_6H_{10}O_5)_xH$, in which n is an integer selected in the range from 2 to 22 and x refers to the mean polymerization level of the glucoside moiety (mono-, di-, tri-, oligo-, and poly-glucosides). These APG's are widely used in household and industrial applications. They are generally derived from renewable raw materials such as glucose derived from corn and plant derived fatty alcohols. These alkyl poly-glucosides generally exhibit a mean polymerisation level of the glucoside moiety ranging from 1 to 1.7, preferably from 1.2 to 1.6 such as from 1.4 to 1.6.

Particularly advantageous alkyl poly-glucosides are $C_{8-10}$ alkyl poly-glucosides consisting essentially of caprylyl ($C_8$) and capryl ($C_{10}$) poly-glucosides. Preferably such caprylyl ($C_8$) and capryl ($C_{10}$) poly-glucosides furthermore exhibit a ratio (%/%), wherein all % are area-% determined by HPLC-MS) of caprylyl ($C_8$) mono-glucoside to capryl ($C_{10}$) mono-glucoside in the range from 3:1 to 1:3, preferably in the range from about 2:1 to 1:2, most preferably in the range from 1.5:1 to 1:1.5. Additionally, such $C_{8-10}$ alkyl poly-glucoside preferably contain no more than 3 wt.-%, more preferably no more than 2 wt.-%, most preferably no more than 1.5 wt.-% of $C_{12}$ alkyl mono-glucoside (as determined by HPLC-MS). It is understood, that such alkyl poly-glucosides are basically free of any higher (i.e. $C_{14-16}$) alkyl polyglucosides.

A particularly advantageous $C_{8-10}$ alkyl poly-glucoside in all embodiments of the present invention is made from glucose derived from corn and $C_8$ and $C_{10}$ fatty alcohols derived from coconut and palm kernel oils, which is e.g. sold as an aqueous dispersion under the tradename Green APG 0810 by Shanghai Fine Chemical.

The amount of the grinding aid in the aqueous dispersion according to the present invention is preferably selected in the range from 1 to 20 wt.-%, more preferably in the range from 2 to 15 wt.-%, most preferably in the range from 5 to 10 wt.-%, based on the total weight of the aqueous dispersion.

Suitable antifoam agents encompass carrier oils, silicone oils and silicone foam inhibitors, hydrophobic silica, hydrophobic fat derivatives and waxes, water-insoluble polymers, amphiphilic components, emulsifiers and coupling agents.

Particularly suitable anti-foam agents to be used in the aqueous dispersion according to the present invention are silicone oils such as in particular polydimethylsiloxanes and/or silicon anti-foam agents such as in particular anhydrous dispersions of pyrogenic or hydrophobized silica in silicone oils such as most in particular simethicone. Most preferably in all embodiments of the present invention the anti-foam agent is simethicone.

The anti-foam agent(s) are preferably used in an amount (total) selected in the range from 0 to 1 wt.-%, more preferably in an amount of 0.01 to 0.2 wt.-%, based on the total weight of the aqueous dispersions.

Particularly suitable wetting agents to be used in the aqueous dispersion according to the present invention are (poly)propyleneglycol(s). Most preferably in all embodiments of the present invention the wetting agent is propyleneglycol.

Such wetting agent(s) are preferably used in an amount (total) selected in the range from 0.1 to 1 wt.-%, more preferably in an amount of 0.2 to 0.6 wt.-%, based on the total weight of the dispersion.

Particularly suitable thickeners to be used in the aqueous dispersion according to the present invention are xanthan gum, gellan gum and/or carboxymethylcellulose. Most preferably in all embodiments of the present invention the thickener is xanthan gum or gellan gum.

Such thickener(s) are preferably used in an amount (total) selected in the range from 0.1 to 1 wt.-%, more preferably in an amount of 0.1 to 0.5 wt.-%, based on the total weight of the aqueous dispersion.

Suitable salts include alkali and earth alkaline salts of phosphate, hydroxide such as e.g. disodium hydrogen phosphate and/or sodium hydroxide.

If present, the salt(s) are used in an amount (total) from 0.01 to 5 wt.-%, preferably from 0.1 to 4 wt.-%, most preferably from 0.5 to 2.5 wt.-%, based on the total weight of the aqueous dispersion.

The topical compositions of the present invention may be produced by physically blending the micronized 1,4-di(benzoxazol-2'-yl)benzene according to the present invention in powder form and a cosmetically acceptable carrier by any conventional method, e.g. by simply stirring the two materials together.

In a preferred embodiment, however, the micronized 1,4-di(benzoxazol-2'-yl)benzene with all the definitions and preferences as given herein is incorporated into the topical composition in the form of an aqueous dispersion thereof as outlined above, which is incorporated into the topical compositions according to standard methods in the art.

Thus, in a preferred embodiment, the present invention relates to topical compositions comprising at least one polar oil and an aqueous dispersion of a micronized 1,4-di(benzoxazol-2'-yl)benzene with all the definitions and preferences as given herein.

In an even more preferred embodiment, said aqueous dispersion consists essentially of the micronized and preferably solid amorphous 1,4-di(benzoxazol-2'-yl)benzene, water and at least one additive selected from the group consisting of a grinding aid, a wetting agent, an anti-foam agent and a thickener as well as mixtures thereof.

Most preferably the at least one further additive in said aqueous dispersion is a $C_{8-16}$ alkyl poly-glucoside and at least one further additive selected from the group consisting of a propyleneglycol, xanthan gum, gellan gum and simethicone as well as mixtures thereof.

Most advantageously in all embodiments according to the present invention said aqueous dispersion consists essentially of
  (i) 20-70 wt.-%, preferably 25-60 wt.-%, based on the total weight of the aqueous dispersion, of the micronized 1,4-di(benzoxazol-2'-yl)benzene with all the preferences and definitions as given herein,
  (ii) 2 to 15 wt.-%, preferably 5 to 10 wt.-%, based on the total weight of the aqueous dispersion, of a $C_{8-16}$ alkyl poly-glucoside with all the preferences and definitions as given above,
  (iii) 0 to 3 wt.-%, preferably 0.1 to 2 wt.-%, based on the total weight of the aqueous dispersion of at least one additive selected from the group consisting of a wetting agent, an anti-foam agent and a thickener as well as mixtures thereof, and
  (iv) 25 to 60 wt.-%, preferably 30 to 45 wt.-%, based on the total weight of the aqueous dispersion, of water.

The term 'consists essentially of' as used according to the present invention means that the amounts of all ingredients such as the ingredients (i) to (iv) sum up to 100 wt.-%. It is, however, not excluded that small amount of impurities or additives may be present which are, for example, introduced via the respective raw materials of the ingredients (i) to (iv).

Most preferably, the aqueous dispersion (I) contains as additives (iii-1) propyleneglycol, (iii-2) one thickener selected from xanthan gum or gellan gum and optionally (iii-3) simethicone.

As the micronized 1,4-di(benzoxazol-2'-yl)benzene according to the present invention significantly reduces the transfer of a topical composition comprising at least one polar oil to surfaces, a further aspect of the present invention is the use of the micronized 1,4-di(benzoxazol-2'-yl)benzene as described and defined herein in a topical composition comprising at least one polar oil for reducing the material transfer to a contacted surface.

The amount of material transfer is determined by determination of the weight of the object (second object) before and after contact. Any weight gain after contact is due to a material transfer from the first to the second object. The reduction of material transfer is determined by comparing compositions according to the inventions with the respective (not according to the invention) composition which does not contain the micronized 1,4-di(benzoxazol-2'-yl)benzene according to the present invention. The reduction is expressed in % of the material transfer of the two measurements.

It has been found that the reduction of more than 20%, even more than 25%, and even up to 45% can be obtained.

The topical composition is applied to a first surface. Said surface is preferably skin, particularly human skin. It has been found that using a porous sponge instead of skin is a good approach for simulate a material transfer from skin to another surface.

The surface of the contacted object (second object) is preferably a glass surface or a plastic or a surface of a fabric.

In case the surface is a fabric, this is very advantages to avoid an unwanted transfer of topical composition to a fabric, particularly to clothes, as the cosmetic composition might stain the fabric.

Particularly, the contacted surface (i.e. surface of second object) is a glass surface.

Most preferably, the contacted surface (i.e. surface of second object) is an optical glass such as used for reading glasses or sunglasses or a display of screen of a smartphone display of a mobile phone, computer device or tablet.

By reducing the material transfer of the topical composition, particularly the problem of marks, particularly finger marks, left on glasses such as optical glasses of instruments or visual glasses when said glass surface is contacted with fingers can be reduced or even avoided. Particularly, this can heavily reduce or even avoid any undesired effects on the light rays transmitted through said glass by said material left on the surface.

Furthermore, marks left on the surface of an aesthetic surface such as of a mirror or a highly glossy or highly mat surface such as a of a top coat of a car or furniture or piece of art, can be strongly reduced. This is very advantageous as such surfaces need a high amount of cleaning maintenance, if they are brought in contact with skin on which topical compositions have been applied, particularly if they are touched by fingers which have been previously in contact with topical compositions.

Marks left on the surface of display units, such as displays of mobile phones, screens, or touch screens of monitors, laptops, mobile phones or tablets can be strongly reduced. As a result of this, the readability can be improved. As the functionality of touch screens depends on surface aspects, the invention helps also to improve constant touch screen functionality without excessive need of cleaning said glass surface.

The reduction of material transfer also heavily reduces the labour and cost involved in the cleaning of said surfaces when they are contacted with skin.

As the micronized 1,4-di(benzoxazol-2'-yl)benzene according to the present invention significantly reduces the transfer of a topical composition comprising at least one polar oil to surfaces, the present invention further relates to
  a method for the use of the micronized 1,4-di(benzoxazol-2'-yl)benzene as described and defined herein in a topical composition comprising at least one polar oil for reducing the transfer of the topical composition to glass or plastic surfaces.
  a method for the use of micronized 1,4-di(benzoxazol-2'-yl)benzene according to the present invention in a topical composition comprising at least one polar oil for reducing the transfer of the topical composition to glass or plastic surfaces.
  a use of a micronized 1,4-di(benzoxazol-2'-yl)benzene as described and defined herein to reduce the transfer of a topical composition comprising at least one polar oil to a surface such as in particular to a glass or plastic surface.
  a method to reduce the transfer of a topical composition comprising at least one polar oil to a surface such as in particular to a glass or plastic surface, said method encompassing the addition of a micronized 1,4-di(benzoxazol-2'-yl)benzene as described and defined herein to a topical composition comprising at least one polar oil.

In a further embodiment, the present invention relates to the topical compositions according to the embodiments described herein for the use as sunscreen, respectively to the use of the topical composition according to the embodiments described herein as sunscreen.

Preferred topical compositions according to the invention are skin care preparations, decorative preparations, and functional preparations.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples of decorative preparations are, in particular, lipsticks, eye shadows, mascaras, dry and moist make-up formulations, rouges and/or powders.

Examples of functional preparations are cosmetic or pharmaceutical compositions containing active ingredients such as hormone preparations, vitamin preparations, vegetable extract preparations, anti-ageing preparations, and/or antimicrobial (antibacterial or antifungal) preparations without being limited thereto.

In a particular embodiment, the topical compositions according to the invention are light-protective preparations (sun care products), such as sun protection milks, sun protection lotions, sun protection creams, sun protection oils, sun blocks or day care creams with a SPF (sun protection factor). Of particular interest are sun protection creams, sun protection lotions, sun protection milks and sun protection preparations.

The topical compositions according to the present invention may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-)type), pickering emulsion, hydrogel, alcoholic gel, lipogel, one- or multiphase solution or vesicular dispersion or other usual forms, which can also be applied by pens, as masks or as sprays.

Preferred topical compositions in all embodiments of the present invention are emulsions which contain an oily phase and an aqueous phase such as in particular O/W, W/O, Si/W, W/Si, O/W/O, W/O/W multiple or a pickering emulsions. Most preferred in all embodiments of the present invention are O/W emulsions as these exhibits a particularly reduced material transfer.

The amount of the oily phase (i.e. the phase containing all oils and fats including the polar oils) present in such emulsions is preferably at least 10 wt.-%, such as in the range from 10 to 60 wt.-%, preferably in the range from 15 to 50 wt.-%, most preferably in the range from 15 to 40 wt.-%, based on the total weight of the topical composition.

The amount of the aqueous phase present in such emulsions is preferably at least 20 wt.-%, such as in the range from 20 to 90 wt.-%, preferably in the range from 30 to 80 wt.-%, most preferably in the range from 30 to 70 wt.-%, based on the total weight of the topical composition.

More preferably, the topical compositions according to the present invention are in the form of an oil-in-water (O/W) emulsion comprising an oily phase dispersed in an aqueous phase in the presence of an O/W- respectively Si/W-emulsifier as such compositions show a significantly pronounced reduction of the transfer of the respective composition to surfaces compared to the respective W/O emulsions. The preparation of such O/W emulsions is well known to a person skilled in the art and illustrated in the examples.

In an advantageous embodiment, the O/W emulsifier is a phosphate ester emulsifier. A particular phosphate ester emulsifier according to the invention is potassium cetyl phosphate e.g. commercially available as Amphisol® K at DSM Nutritional Products Ltd Kaiseraugst.

The at least one O/W respectively Si/W emulsifier is preferably used in an amount of 0.5 to 10 wt.-% such as in particular in the range from 0.5 to 5 wt.-% such as most in particular in the range from 0.5 to 4 wt.-% based on the total weight of the composition.

A suitable W/O- or W/Si-emulsifiers is polyglyceryl-2-dipolyhydroxystearat. The at least one W/O emulsifier is preferably used in an amount of about 0.001 to 10 wt.-%, more preferably in an amount of 0.2 to 7 wt.-% with respect to the total weigh of the composition.

The topical compositions according to the present invention furthermore advantageously contain at least one co-surfactant such as e.g. selected from the group of mono- and diglycerides and/or fatty alcohols. The co-surfactant is generally used in an amount selected in the range from 0.1 to 10 wt.-%, such as in particular in the range from 0.5 to 6 wt.-%, such as most in particular in the range from 1 to 5 wt.-%, based on the total weight of the composition. Particular suitable co-surfactants are selected from the list of alkyl alcohols such as cetyl alcohol (Lorol C16, Lanette 16), cetearyl alcohol (Lanette O), stearyl alcohol (Lanette 18), behenyl alcohol (Lanette 22), glyceryl stearate, glyceryl myristate (Estol 3650), hydrogenated coco-glycerides (Lipocire Na10) as well as mixtures thereof.

The compositions in form of O/W emulsions according to the invention can be provided, for example, in all the formulation forms for O/W emulsions, for example in the form of serum, milk or cream, and they are prepared according to the usual methods. The compositions which are subject-matters of the invention are intended for topical application and can in particular constitute a dermatological or cosmetic composition, for example intended for protecting human skin against the adverse effects of UV radiation (antiwrinkle, anti-ageing, moisturizing, anti-sun protection and the like).

According to an advantageous embodiment of the invention the compositions constitute cosmetic composition and are intended for topical application to the skin.

Finally, a subject-matter of the invention is a method for the cosmetic treatment of keratinous substances such as in particular the skin, wherein a topical composition as defined herein is applied to the said keratinous substances such as in particular to the skin. The method is in particular suitable to protect the skin against the adverse effects of UV-radiation such as in particular sun-burn and/or photoageing.

In accordance with the present invention, the compositions according to the invention may comprise further ingredients such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self-tanning, soothing, as well as agents to improve elasticity and skin barrier and/or further UV-filter substances and carriers and/or excipients or diluents conventionally used in topical compositions. If nothing else is stated, the excipients, additives, diluents, etc. mentioned in the following are suitable for topical compositions according to the present invention. The necessary amounts of the cosmetic and dermatological adjuvants and additives can, based on the desired product, easily be determined by the skilled person. The additional ingredients can either be added to the oily phase, the aqueous phase or separately as deemed appropriate. The mode of addition can easily be adapted by a person skilled in the art.

The cosmetically active ingredients useful herein can in some instances provide more than one benefit or operate via more than one mode of action.

The topical cosmetic compositions of the invention can also contain usual cosmetic adjuvants and additives, such as preservatives/antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, pigments or nanopigments, e.g. those suited for providing a photoprotective effect by physically blocking out ultraviolet radiation, or any other ingredients usually formulated into cosmetic compositions.

Such cosmetic ingredients commonly used in the skin care industry, which are suitable for use in the compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp),withoutbeinglimitedthereto.

The necessary amounts of the cosmetic and dermatological adjuvants and additives can—based on the desired product—easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The topical compositions according to the invention in general have a pH in the range from 3 to 10, preferably a pH in the range from 4 to 8 and most preferably a pH in the range from 4 to 7. The pH can easily be adjusted as desired with suitable acids such as e.g. citric acid or bases such as NaOH according to standard methods in the art.

The topical compositions according to the invention may further contain one or more emollients which soothe and soften the skin. As an example, the emollient may be dicaprylyl carbonate. Further emollients are silicone (dimethicone, cyclomethicone), vegetable oils (grape seed, sesame seed, jojoba, etc.), butters (cocoa butter, shea butter), alcohols and petrolatum derivatives (petroleum jelly, mineral oil).

The cosmetic compositions according to the present invention advantageously comprise preservatives or preservative booster. When present, the preservative respectively preservative booster is preferably used in an amount of 0.01 to 2 wt.-%, more preferably in an amount of 0.05 to 1.5 wt.-%, most preferably in an amount of 0.1 to 1.0 wt.-%, based on the total weight of the composition. It is particularly preferred, that the cosmetic compositions according to the invention does not contain any preservatives selected from the group of parabens and/or methylisothiazolidine.

The following examples are provided to further illustrate the compositions and effects of the present invention. These examples are illustrative only and are not intended to limit the scope of the invention in any way.

EXAMPLES

1. Preparation of Micronized 1,4-di(benzoxazol-2'-yl)benzene

1.1 General Methods

All particles sizes have been determined by laser diffraction with a Malvern Mastersizer 2000 according to the method as outlined in ISO 13320:2009 and/or a Coulter Delsa Nano S (dynamic laser scattering).

Differential scanning calorimetry (DSC) was performed using Mettler Toledo DSC1 (temperature range from 25° C. to 400° C.; heating rate: 4° C./min; air atmosphere, 2-3 mg samples, average from 2 measurements).

X-ray diffraction patterns were recorded using a Bruker D8 Advance powder X-ray diffractometer in reflection (Bragg-Brentano) geometry. The PXRD diffractometer was equipped with a LynxEye detector. The samples were generally prepared without any special treatment other than the application of slight pressure to get a flat surface. Silicon single crystal sample holder for polymorph screening, 1.0 mm depth. Samples were measured uncovered. The tube voltage was 40 kV and current was 40 mA. A variable divergence slight was used with a 3° window. The step size was 0.02 °2θ with a step time of 37 seconds. The samples were rotated at 0.5 rps during the measurement.

E 1/1 values were determined with a UV/(vis) spectrometer (Perkin Elmer Lambda 650S) at 320 nm and a baseline correction according to the following formula: E 1/1=(E 1/1 @ 320 nm)−(E 1/1 @ 650 nm).

The UVB:UVA ratio was determined by measuring the UV-spectra of the respective micronized UV-filter dispersed in water at a concentration of 0.001% (w/v) active and calculating the ratio by dividing the area-% from 290 to 319 nm (UVB) through the area-% from 320 to 400 nm (UVA).

1.2 Preparation of Coarse Particles of Solid Amorphous 1,4-di(benzoxazol-2'-yl)benzene (DBO-400 (A))

A mixture of 702 g polyphosphoric acid and 4.28 ml methanesulfonic acid was heated to 90° C. 65 g terephthalic acid and 107 g 2-aminophenol were added. The mixture was stirred under inert atmosphere at 180° C. for 8 hours and then transferred to ice water. The precipitated product was filtered and washed with water and acetic acid. The precipitate was dispersed in water and the pH adjusted to 8.0 with sodium hydroxide, filtered and washed with water. The crude product was suspended in a mixture of toluene and 1-butanol 3.3:1, stirred at 85° C. for one hour, filtered, washed with diethyl ether, and dried. The resulting coarse particles of solid amorphous 1,4-di(benzoxazol-2'-yl)benzene exhibited a particle size Dn50 of 380 nm (Malvern).

1.3 Preparation of an Aqueous Dispersion of Solid Amorphous 1,4-di(benzoxazol-2'-yl)benzene (DBO-200 Dispersion (A))

A suspension of 175 g of DBO-400 obtained as outlined in (1), 324 g of water and 65 g Green APG 0810 was prepared. Afterwards the suspension was milled for 2 h with a LabStar laboratory mill using yttrium-stabilized zirconium oxide grinding beads (0.3 mm, from Tosoh Ceramic, Japan) and cooling of the milling chamber (−12° C. brine). After removal of the grinding beads, a 30% aqueous dispersion of micronized 1,4-di(benzoxazol-2'-yl)benzene was obtained.

Particle size:
Malvern: Dn50 186 nm (Dn10=126 nm, Dn90=355 nm)
Coulter: Mean value (intensity distribution): 171 nm
E 1/1: 839
DSC: onset temperature: 350° C.; heat capacity: 132 J/g.
Ratio UVB:UVA: 0.49
X-ray: FIG. 1, line 4

1.4 Preparation of an Aqueous Dispersion of Crystalline 1,4-di(benzoxazol-2'-yl)benzene (DBO-200 Dispersion (C))

After recrystallisation of coarse particles obtained as outlined in (1.2) from o-dichlorobenzene and drying 73.0% of crystalline 1,4-di(benzoxazol-2'-yl)benzene was obtained, which was subsequently milled in analogy to the process outlined in (1.3). After removal of the grinding beads a 30% aqueous dispersion of crystalline 1,4-di(benzoxazol-2'-yl)benzene was obtained.
Particle size:
Coulter: Mean value (intensity distribution): 193 nm
E 1/1: 719
DSC: Onset temperature: 352° C.; heat capacity: 153 J/g
Ratio UVB:UVA: 0.35
X-ray: FIG. 1, line 2

1.5 Preparation of an Aqueous Dispersion of Coarse Solid Amorphous 1,4-di(benzoxazol-2'-yl)benzene (DBO-400 Dispersion (A))

A suspension of 1.8 g of DBO-400 obtained as outlined in (1), 3.51 g of water and 0.69 g of Green APG 0810 was prepared. Afterwards the suspension was mixed at ambient temperature (22° C.) with a magnetic mixture until a homogenous dispersion was obtained. After removal of the magnetic stir bar a 30% aqueous dispersion of micronized 1,4-di(benzoxazol-2'-yl)benzene having a mean particle size Dn50 of 380 nm (Malvern) was obtained.

2. Material Transfer

The material transfer has been determined with the sponge test as outlined in the following:
- Cut a sponge cloth (Weitawip Claire, from Weita AG: cellulose/cotton fiber mixture, 200 g/m$^2$, 5 mm thickness) into pieces of 76 mm×26 mm
- Tare the sponge sample
- Apply 400 mg of the respective sample (=cosmetic composition) and distribute homogenously all over the sponge surface of 76 mm×26 mm
- Weigh the sponge with the applied sample
- Tare a microscope slide (glass plate 76 mm×26 mm×1 mm)
- Put the microscope slide (glass plate) on top of the sponge, on which a balance weight of 500 g (height: 6.3 cm, diameter at area of contact: 3.7 cm) is placed for 10 seconds to apply a specific pressure to the sample
- Remove cautiously vertically the microscope slide
- Weigh the removed microscope slide and determine accordingly the amount of sample transferred to the glass plate
- Repeat the test for each composition 10 times to receive an average value (mean value) for each sample.

2.1 Material Transfer in Dependence of the Particle Size and Formulation Type The formulations as outlined in table 1 have been prepared according to standard methods in the art. Afterward the material transfer was assessed as outlined above.

TABLE 1

| | Transfer resistance (I) | | | | | | | |
|---|---|---|---|---|---|---|---|---|
| | INCI | | | | | | | |
| | Inv-1 O/W | Ref-1 O/W | Inv-2 O/W | Ref-2 O/W | Inv-3 O/W | Ref-3 O/W | Inv-4 W/O | Ref-4 W/O |
| | Wt % | | | | | | | |
| Potassium Cetyl Phosphate O/W emulsifier | 1.5 | 1.5 | 1.5 | 1.5 | 1.5 | 1.5 | | |
| Polyglyceryl-2-dipolyhydroxystearate | | | | | | | 5.0 | 5.0 |
| Cetyl alcohol | 3.0 | 3.0 | 3.0 | 3.0 | 3.0 | 3.0 | | |
| Cetearyl alcohol | 1.0 | 1.0 | 1.0 | 1.0 | 1.0 | 1.0 | | |
| Microcristalline wax | | | | | | | 2.0 | 2.0 |
| Isohexadecane (polarity index 43.8 mN/m) | 8.0 | 8.0 | | | | | | |
| Caprylic/Capric triglyceride (polarity index 21.3 mN/m) | | | 8.0 | 8.0 | | | 15.0 | 15.0 |
| Diisopropyl Adipate (polarity index 11.6 mN/m) | | | | | 8.0 | 8.0 | | |
| Aqua | Ad 100 | | | | | | | |
| Glycerin | 3.0 | 3.0 | 3.0 | 3.0 | 3.0 | 3.0 | 4.0 | 4.0 |
| Xanthan Gum | 0.3 | 0.3 | 0.3 | 0.3 | 0.3 | 0.3 | | |
| Magnesium sulfate heptahydrate | | | | | | | 1.0 | 1.0 |
| preservative | 1.0 | 1.0 | 1.0 | 1.0 | 1.0 | 1.0 | 0.5 | 0.5 |
| DBO-200 dispersion (A) | 2.4* | — | 2.4* | — | 2.4* | — | 2.4* | — |
| DBO-400 dispersion (A) | — | 2.4* | — | 2.4* | — | 2.4* | — | 2.4* |
| Transfer [%] | 1.00 | 1.38 | 0.78 | 1.20 | 0.71 | 0.86 | 1.29 | 2.25 |
| Difference vs Reference# | -28% | | -35% | | -17% | | -43% | |

*Based on active
(Transfer DBO-400 dispersion − Transfer DBO-200 dispersion)/Transfer DBO-400 dispersion * 100%)

As can be retrieved from the table, the addition of the micronized 1,4-di(benzoxazol-2'-yl)benzene according to the present invention significantly reduced the amount of the cream transferred to the glass surface compared to the references rendering the glass surfaces less smeary compared to the references. The use of more polar oils was even more advantageous. Additionally, the transfer is significant lower in O/W formulations than in W/O formulations.

2.2 Material Transfer in Dependence of the Polarity Index of the Oil

In analogy to the O/W formulation outlined in table 1, further O/W emulsions with additional polar oils were prepared using the DBO-200 (A) dispersion. The result of the material transfer assessments thereof is outlined in table 2.

TABLE 2

Transfer resistance (II)

| Oil | polarity index mN/m | transfer [%] |
|---|---|---|
| Isohexadecane | 43.8 | 1.00 |
| Isocetyl Stearate | 36.2 | 0.60 |
| Dicaprylyl Carbonate | 31.7 | 0.44 |
| Cetearyl Isononanoate | 28.6 | 0.57 |
| Caprylic/Capric Triglyceride | 21.3 | 0.78 |
| Diiso propyl adipate | 11.6 | 0.71 |
| C12-13 Alkyl Tartrate | 7.1 | 0.53 |
| Cocoglycerides | 5.1 | 0.51 |

As can be retrieved from table 2, best results, i.e. the least material transfer is obtained for polar oils having a polarity index selected in the range from 1 to 10 mN/m and in the range from 25 to 40 mN/m.

2.3 Material Transfer in Dependence of the Formulation Type

In analogy to the O/W respectively W/O formulation outlined in table 1 further O/W respectively W/O emulsions were prepared using the DBO-200 (A) dispersion and the polar oil as outlined in table 3. Afterwards the material transfer was assessed as described above. The result thereof is outlined in table 3.

TABLE 3

Transfer resistance (III)

| | | Formulation type | | |
|---|---|---|---|---|
| | | O/W | O/W | W/O |
| Oil | polarity index mN/m | transfer [%] 8% oil | transfer [%] 15% oil | transfer [%] 15% oil |
| Parrafinum liquidum | 46.7 | — | — | 1.02 |
| Hydrogenated Polyisobutene | 44.7 | — | — | 1.18 |
| Dicaprylyl Carbonate | 31.7 | 0.44 | 0.55 | 0.79 |
| Caprylic/Capric Triglyceride | 21.3 | 0.78 | — | 1.29 |

As can be retrieved from table 3, W/O emulsions generally exhibit a significantly higher material transfer compared to the respective O/W emulsions, also at same oil content.

3. UV-Protection

The formulations as outlined in table 4 have been prepared according to standard methods in the art. Afterward the in vitro SPF was assessed directly after manufacturing (t0) and after 1-month storage at RT (t1). The in vitro SPF test was performed on PMMA plates (WW5 from Schönberg, 5 cm×5 cm, roughness of 5 μm): 32.5 mg of the respective formulation (i.e. 1.3 mg/cm$^2$) were applied homogenously onto the PMMA plates and dried for 15 minutes.

The in vitro SPF was determined using Labsphere 2000 UV Transmittance Analyzer: each PMMA plate was measured 9 times at different points on the plate resulting in 27 data points. The result is calculated as the average of these 27 data points.

TABLE 4 in vitro SPF

| Ingredient | Wt.-% | Wt.-% |
|---|---|---|
| Potassium Cetyl Phosphate | 1.8 | 1.8 |
| Glyceryl Stearate | 2.0 | 2.0 |
| Stearyl Alcohol | 2.5 | 2.5 |
| Isopropyl Myristate | 2.0 | 2.0 |
| C12-15 Alkyl Benzoate | 5.0 | 5.0 |
| Caprylic/Capric Triglyceride | 5.0 | 5.0 |
| Xanthan Gum | 0.4 | 0.4 |
| Aqua | Ad 100 | Ad 100 |
| Preservative | 1.0 | 1.0 |
| amorphous DBO (30% active) (DBO-200 dispersion (A) | 3* | |
| crystalline DBO (30% active) (DBO-200 dispersion (C) | | 3* |
| In vitro SPF @ t0 | 9.1 | 6.5 |
| In vitro SPF @ t1 | 8.7 | 2.9 |
| Critical wavelength | 379 | 382 |

*based on the active (i.e. 10 wt.-% of the respective dispersion)

As can be retrieved from table 4 the use of solid amorphous DBO results in a significantly higher SPF compared to the respective crystalline form. Furthermore, such formulations are more storage stable as reflected by an unchanged in vitro SPF after 1-month storage @ RT for the solid amorphous form compared to a significantly reduced SPF after 1-month storage @ RT for of the respective crystalline form.

The invention claimed is:

1. A topical composition comprising: at least one polar oil having a polarity index of less than 55 mN/m, wherein the at least one polar oil is present in an amount from 1 to 30 wt %, and micronized solid amorphous 1,4-di(benzoxazol-2'-yl)benzene having a mean particle size Dn50 of at most 300 nm as determined by laser diffraction, wherein the micronized solid amorphous 1,4-di(benzoxazol-2'-yl)benzene is present in an amount from 0.1 to 20 wt %.

2. The topical composition according to claim 1, wherein the at least one polar oil has a polarity index selected in the range from 1 to 40 mN/m.

3. The topical composition according to claim 2, wherein the at least one polar oil has a polarity index in a range from 1 to 10 mN/m and/or in a range from 25 to 40 mN/m.

4. The topical composition according to claim 3, wherein the at least one polar oil is selected from the group consisting of isocetyl stearate, dicaprylyl carbonate, cetearyl isononanoate, C12-13 alkyl tartrate, cocoglycerides and mixtures thereof.

5. The topical composition according to claim 1, wherein the micronized 1,4-di(benzoxazol-2'-yl)benzene has a mean particle size $D_n50$ selected in the range from 50 to 300 nm, more preferably in the range from 120 to 280 nm, most preferably in the range from 150 to 220 nm.

6. The topical composition according to claim 1, wherein the micronized solid amorphous 1,4-di(benzoxazol-2'-yl) benzene has a specific absorbance E 1/1 at 320nm of ≥780.

7. The topical composition according to claim 1, wherein the micronized solid amorphous 1,4-di(benzoxazol-2'-yl) benzene is incorporated into the topical composition in the form of an aqueous dispersion thereof.

8. The topical composition according to claim 1, wherein the topical composition is an emulsion containing an oily phase and an aqueous phase.

9. The topical composition according to claim 8, wherein the oily phase is present in the emulsion in an amount from 10 to 60 wt. %, based on the total weight of the topical composition.

10. The topical composition according to claim 1, wherein the topical composition is in the form of an oil-in-water (O/W) emulsion comprising an oily phase dispersed in an aqueous phase in the presence of an O/W emulsifier.

11. The topical composition according to claim 10, wherein the O/W emulsifier is a phosphate ester emulsifier.

12. The topical composition according to claim 11, wherein the phosphate ester emulsifier is a cetyl phosphate emulsifier.

13. The topical composition according to claim 1, wherein the at least one polar oil is present in an amount in the range from 2 to 25 wt. %, based on the total weight of the topical composition.

14. The topical composition according to claim 1, wherein the at least one polar oil is present in an amount in the range from 3 to 20 wt. %, based on the total weight of the topical composition.

15. The topical composition according to claim 1, wherein the micronized solid amorphous 1,4-di(benzoxazol-2'-yl) benzene is present in an amount from 0.2 to 15 wt. , based on the total weight of the topical composition.

16. The topical composition according to claim 1, wherein the micronized solid amorphous 1,4-di(benzoxazol-2'-yl) benzene is present in an amount from 0.3 to 10 wt. %, based on the total weight of the topical composition.

17. The topical composition according to claim 1, wherein the micronized solid amorphous 1,4-di(benzoxazol-2'-yl) benzene has a mean particle size $D_n50$ selected in a range from 120 to 280 nm.

18. The topical composition according to claim 1, wherein the micronized solid amorphous 1,4-di(benzoxazol-2'-yl) benzene has a mean particle size $D_n50$ selected in a range from 150 to 220 nm.

19. The topical composition according to claim 8, wherein the oily phase is present in the emulsion in an amount from 15 to 50 wt. %, based on the total weight of the topical composition.

20. The topical composition according to claim 8, wherein the oily phase is present in the emulsion in an amount from 15 to 40 wt. %, based on the total weight of the topical composition.

* * * * *